United States Patent
Jones et al.

(10) Patent No.: US 10,416,784 B2
(45) Date of Patent: Sep. 17, 2019

(54) SYSTEMS AND METHODS FOR DETECTING TRAFFIC IN A SHOPPING FACILITY

(71) Applicant: Walmart Apollo, LLC, Bentonville, AR (US)

(72) Inventors: Nicholaus A. Jones, Fayetteville, AR (US); Robert J. Taylor, Rogers, AR (US); Aaron J. Vasgaard, Rogers, AR (US); Matthew A. Jones, Bentonville, AR (US)

(73) Assignee: Walmart Apollo, LLC, Bentonville, AR (US)

( * ) Notice: Subject to any disclaimer, the term of this patent is extended or adjusted under 35 U.S.C. 154(b) by 156 days.

(21) Appl. No.: 15/609,085

(22) Filed: May 31, 2017

(65) Prior Publication Data

US 2017/0344129 A1 Nov. 30, 2017

Related U.S. Application Data

(60) Provisional application No. 62/343,296, filed on May 31, 2016.

(51) Int. Cl.
*G06F 3/03* (2006.01)
*A61B 5/11* (2006.01)
(Continued)

(52) U.S. Cl.
CPC .......... *G06F 3/0325* (2013.01); *G06F 16/487* (2019.01); *G06Q 30/00* (2013.01);
(Continued)

(58) Field of Classification Search
CPC ................. G06F 3/0325; G06F 16/487; G06F 17/30041; G06Q 30/00; A61B 5/1113; A61B 5/1122; A61B 2503/12
(Continued)

(56) References Cited

U.S. PATENT DOCUMENTS

| 5,138,638 A | 8/1992 | Frey |
| 7,930,204 B1 | 4/2011 | Sharma |

(Continued)

OTHER PUBLICATIONS

Vargheese, Rajesh; "An IoT/IoE Enabled Architecture Framework for Precision on Shelf Availability"; IEEE; Oct. 2014; pp. 6.
(Continued)

*Primary Examiner* — Dinh T Le
(74) *Attorney, Agent, or Firm* — Fitch, Even, Tabin & Flannery LLP

(57) ABSTRACT

In some embodiments, apparatuses and methods are provided herein useful for detecting traffic in a shopping facility. A system for detecting traffic in a shopping facility comprises: a plurality of light emitters coupled to motion sensors configured to emit light when motion is detected by the motion sensor; a light detector having a field of view including at least one of the plurality of light emitters; a database; and a control circuit configured to obtain data from the light detector relating to light emitted from the light emitters, estimate a location of the light emitted from the light emitters based on location data associated with the light emitter stored in the database, and track a path of a customer based on successive light emissions from the light emitters.

14 Claims, 3 Drawing Sheets

(51) Int. Cl.
    *G06F 16/487*    (2019.01)
    *G06T 7/292*     (2017.01)
    *G06Q 30/00*    (2012.01)

(52) U.S. Cl.
    CPC ............. *G06T 7/292* (2017.01); *A61B 5/1113* (2013.01); *A61B 5/1122* (2013.01); *A61B 2503/12* (2013.01)

(58) Field of Classification Search
    USPC .......................................................... 377/6
    See application file for complete search history.

(56) References Cited

U.S. PATENT DOCUMENTS

| | | |
|---|---|---|
| 7,996,281 B2 | 8/2011 | Alvarez |
| 8,564,661 B2 | 10/2013 | Lipton |
| 9,031,858 B2 * | 5/2015 | Angell ................... G06Q 30/02 705/14.52 |
| 9,104,430 B2 * | 8/2015 | Chu ....................... G06F 9/4411 |
| 9,503,539 B1 * | 11/2016 | Trundle ............. G08B 21/0423 |
| 9,600,982 B2 * | 3/2017 | MacIntosh |
| 2005/0027443 A1 | 2/2005 | Cato |
| 2006/0215022 A1 | 9/2006 | Damabhorn |
| 2007/0067203 A1 | 3/2007 | Gil |
| 2008/0215391 A1 | 9/2008 | Dowling |
| 2009/0326807 A1 | 12/2009 | Ramaswamy |
| 2013/0229263 A1 | 9/2013 | Graczyk |
| 2015/0338548 A1 | 11/2015 | Cortelyou |
| 2015/0356610 A1 | 12/2015 | Ponoth |

OTHER PUBLICATIONS

PCT; App. No. PCT/US2017/35110 ; International Search Report and Written Opinion dated Aug. 29, 2017.

* cited by examiner

SYSTEMS AND METHODS FOR DETECTING TRAFFIC IN A SHOPPING FACILITY

RELATED APPLICATION

This application claims the benefit of U.S. Provisional Application No. 62/343,296 filed on May 31, 2016, which is incorporated herein by reference in its entirety.

TECHNICAL FIELD

The field of this invention relates generally to detecting traffic in a shopping facility.

BACKGROUND

In modern retail environments, there is a need to improve the customer experience. Part of the customer experience is the convenience to customer. Further, the customer experience at the shopping facility can have significant effects on current sales. Providing a pleasant or improved customer experience can lead to customer satisfaction and repeat returns to the shopping location.

There are many ways to improve customer experience. For example, ready access to products and convenience to collecting products can lead to increased customer visits and customer loyalty. The shopping facility can affect customer experience based, in part, on finding products of interest, access to a shopping facility, and/or congestion within the shopping facility. Accordingly, it can be advantageous to improve the customers' shopping experience.

BRIEF DESCRIPTION OF THE DRAWINGS

Disclosed herein are embodiments of apparatuses and methods for detecting traffic in a shopping facility. This description includes drawings, wherein.

Figure 1:
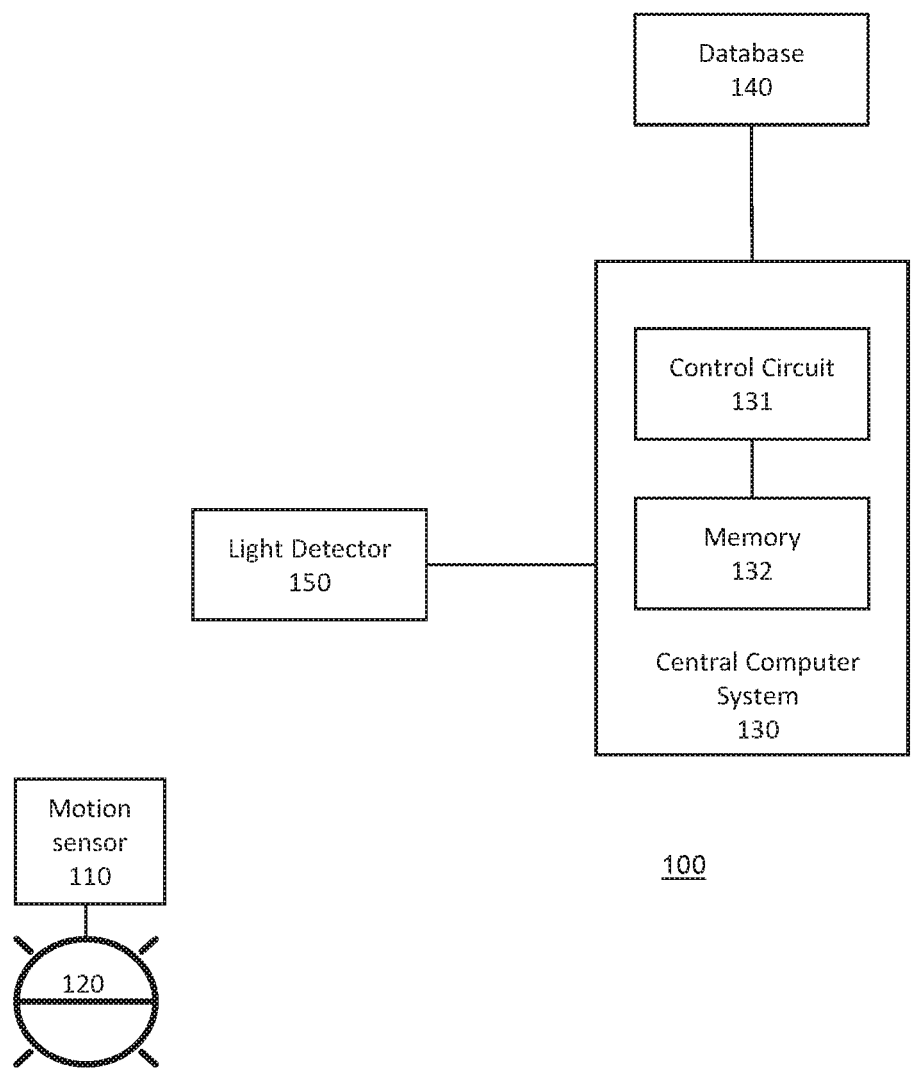
FIG. 1 is a block diagram of a system in accordance with several embodiments.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

The following description is not to be taken in a limiting sense, but is made merely for the purpose of describing the general principles of exemplary embodiments. Reference throughout this specification to "one embodiment," "an embodiment," "some embodiments", "an implementation", "some implementations", or similar language means that a particular feature, structure, or characteristic described in connection with the embodiment is included in at least one embodiment of the present invention. Thus, appearances of the phrases "in one embodiment," "in an embodiment," "in some embodiments", "in some implementations", and similar language throughout this specification may, but do not necessarily, all refer to the same embodiment.

Generally speaking, pursuant to various embodiments, systems, apparatuses and methods are provided herein useful for detecting traffic in a shopping facility. Embodiments may include one more light emitters, each light emitter coupled to a motion sensor configured to detect motion of an approaching customer, such that the one or more light emitters are configured to emit light when motion is detected by its associated motion sensor. A light detector having a field of view including at least one of the light emitters and configured to detect light from the light emitter may be included, and a database configured to store data obtained from the light detector and location data associated with the light emitters may also be included. Embodiments may also include a control circuit coupled to the light detector and the database, the control circuit configured to obtain data from the light detector relating to light emitted from each of the light emitters and estimate a location of the light emitted from each of the light emitters based on location data associated with each of the light emitters stored in the database.

Typically, paths that customers take while shopping in a store are not known to the store operator. Knowledge of where customers go and how long customers dwell in specific areas of the store can be reviewed to improve store layout and product placement. In some embodiments, the locations and traffic patterns of customers can be estimated and/or tracked by placing one or more motion-activated light emitters around the sales floor and detecting the occurrences, durations, and patterns of the light emitted when customers activate the one or more motion-activated light emitters upon approach. The system may then estimate and/or determine frequently used paths, dwell times at different locations, point of sale (POS) processing time, speed of shopping, and/or where work is being completed, etc. in the shopping space based on tracking customers' traffic patterns. The light emitted may be visible light which may serve to also illuminate one or more retail products in the shopping facility, or the light emitted may be non-visible light. In some embodiments, light emitters may be configured to emit different wavelengths of light. The system may further trigger actions for locations that are heavily shopped and may need customer service (e.g. more deli associates, more cashiers, more produce rotation, etc.).

In some embodiments, a store worker's location and/or path of travel may be estimated by comparing a scan from the handheld device carried by the store worker with stored scan data. In some embodiments, the system may determine if the store worker is present when the light emitter is activated by comparing the store worker's location to data obtained from the light detector and the light emitter.

Referring now to FIG. 1, a system for tracking traffic in a shopping facility is shown. The system 100 includes a central computer system 130, a database 140, and a light detector 150 for detecting light emitted from a light emitter 120, which may be coupled to a motion sensor 110.

The motion sensor 110 may be configured to detect motion from an approaching person within a predetermined distance using any active or passive motion sensing technology, such as, for example, infrared, ultrasonic, microwave, and combinations thereof. The motion sensor 110 may be positioned in any location in a shopping facility. For example, the motion sensor 110 may be installed in the ceiling, pillars, beams, modules, display shelves, etc. of the shopping facility. The motion sensor 110 may be communicatively coupled to the light emitter 120 and may be configured to cause the light emitter 120 to emit light when the motion sensor 110 detects motion. The motion sensor 110 may be coupled to the light emitter 120 via a wired and/or wireless signal connections. In some embodiments, the light emitter 120 may be integrated with the motion sensor 110. In some embodiments, the light emitter 120 and the motion sensor 110 may be battery powered.

The light emitter 120 may be configured to emit any color or wavelength of visible light or non-visible light. In some embodiments, for example, in low traffic areas of the store, the light emitted from the light emitter 120 may be visible light and may be positioned to illuminate one or more retail products adjacent to the light emitter 120 when motion is detected by the motion sensor 110. In some embodiments, the light emitter 120 may be configured to emit different wavelengths of light based on the number of customers the motion sensor 110 detects at any given time. For example, when a first person approaches the motion sensor 110, the light emitter 120 may emit a first wavelength of light. When a second person approaches the motion sensor 110 while first person is still present, the light emitter 120 may emit a second wavelength of light in place of, or in addition to, the first wavelength of light. In some embodiments, the light emitter 120 may be configured to emit different patterns of light based on the number of customers the motion sensor 110 detects at any given time. In some embodiments, the light emitter 120 may be configured to emit light for a predetermined length of time. In other embodiments, the light emitter 120 may be configured to emit light for a length of time that the motion sensor detects a continuous motion. The light emitter 120 may be positioned in any location in a shopping facility. For example, the light emitter 120 may be installed in the ceiling, pillars, beams, modules, display shelves, etc. of the shopping facility. Some embodiments may include a plurality motion sensors 110 coupled to a plurality of light emitters 120 positioned at predetermined locations throughout the shopping facility. In some embodiments, each light emitter 120 in the plurality of light emitters may emit one or more different wavelengths of light such that each location of each light emitter 120 is associated with one or more different wavelengths of light.

The light detector 150 may generally be configured to capture light in a shopping facility and transmit the captured data to the central computer system 130. The light detector 150 may comprise any luminosity detector or imaging device that is capable of detecting light. In some embodiments, the light detector 150 may comprise a video imaging device. The light detector 150 may have a field of view including one or more of the light emitter 120. In some embodiments, the light detector 150 may comprise an array of light detectors positioned throughout a shopping facility, which may, in some cases, detect one or more different wavelengths of light. The light detector 150 may comprise stationary light detectors installed in the shopping facility. For example, the light detector 150 may be installed in the ceiling, pillars, beams, modules, display shelves, etc. of a shopping facility. In some embodiments, the light detector 150 may be configured to detect specific wavelengths of light which may be emitted by the light emitter 120.

The central computer system 130 may include a control circuit 131 and a memory 132 and may generally be any processor-based device such as one or more of a computer system, a server, a networked computer, a cloud-based server, etc. The control circuit 131 may comprise a central processing unit, a processor, a microprocessor, and the like. The control circuit 131 may be configured to execute computer readable instructions stored on the memory 132. The memory 132 may comprise volatile and/or non-volatile computer readable storage memory and have stored upon it a set of computer readable instructions which, when executed by the control circuit 131, causes the system to obtain data from the light detector 150 captured from the light emitter 120. The central computer system 130 may be coupled to the light detector 150 via a wired and/or wireless signal connections. In some embodiments, the central computer system 130 may be configured to process the data collected by the light detector 150 and to compare the data to stored location data associated with the light emitter 120 to estimate a location of the light emitter 120, thereby allowing the system to ascertain the presence and location of one or more customers in the vicinity of the light emitter 120. The central computer system 130 may determine the location of each light emitter 120 based, for example, on the variance in each of the emitted light's spectra, strobe rate, and the like, which may be stored in database 140. In some embodiments, the central computer system 130 may estimate a location of one or more light emitters 120 using a video imaging device, which may determine a distance and source of the emitted light for each light emitter 120. In some embodiments, the video imaging device may be the light detector 150. The estimated location(s) of the one or more light emitters 120 may be stored in the video imaging device and/or in one or more databases.

In some embodiments, the central computer system 130 may be configured to estimate customer traffic patterns in an area adjacent to the light emitter 120 based at least on how often the light emitter is activated to emit light. In some embodiments, the central computer system 130 may be configured to estimate customer traffic patterns and/or customer density based on the number of different wavelengths and/or patterns of light emitted from one or more light emitters 120 at any given time or during any given duration. In some embodiments, the central computer system 130 may be configured to track a path of a customer based on successive light emissions from a plurality of light emitters 120 positioned throughout the shopping facility. For example, as a customer approaches a first aisle in a shopping facility, a first light emitter 120 may emit a first light in response to the approaching customer. The light emitted from the first light emitter 120 may be a short burst of light, or the light emitter 120 may remain lit for as long as the motion sensor 110 coupled to the light emitter 120 detects motion from the customer. When the customer moves from the first aisle to a second aisle, a second light emitter 120 may emit a second light in response to the approaching customer. The light detector 150 captures the light emissions from the first and second light emitters 120 and estimates the locations of the first and second light emitters 120 based on stored location data, allowing the central computer system 130 to track the customer throughout the store. In cases where each light emitter 120 emits one or more different wavelengths of light, the central computer system 130 may automatically determine the location of each light emitter 120 based on known locations associated with each wavelength of light. Detecting a succession of light emissions from a plurality of light emitters 120 throughout the shopping facility not only allows for the tracking of a single customer's path throughout the shopping facility, but the aggregation of such data from multiple customers allows for the creation of traffic patterns and heat maps of activity throughout the store, which may be valuable for store management and marketing purposes. In some embodiments, the central computer system 130 may be further configured to estimate dwell time of a customer based on the length of time that the light emitter emits light. In some embodiments, the customer's path of travel may be stored in database 140.

In some embodiments, the central computer system 130 may be configured to automatically generate one or more alerts and/or tasks based on the tracked location(s) and/or route(s) of customer(s). For example, the central computer system 130 may determine one or more heavily trafficked areas and instruct a motorized unit and/or a store associate to survey the area to ensure the area is clean and/or sufficiently stocked. In another example, the central computer system 130 may determine one or more areas with unusually low traffic and instruct a motorized unit and/or a store associate to investigate for the presence of spills or other types of obstructions. In some embodiments, the system may aggregate a plurality of estimated customer traffic routes to determine sections needing attention and/or possible modification.

In some embodiments, the central computer system 130 may compare customer traffic patterns with point of sale data to determine if the point of sale data correlates to the customer traffic patterns. For example, in some embodiments, the central computer system 130 may match the customer with a checkout receipt based on the time that the customer approaches a checkout terminal. The central computer system 130 may then compare the items purchased during that shopping trip with the route and the dwell time of the customer. If the customer dwells at a section of the store for an extended period of time but no item from that section of the store is purchased, the system may mark the section as a section that needs attention. In some embodiments, the system may aggregate a plurality of customer traffic routes to determine sections needing attention and/or possible modification. Generally, the estimated customer traffic patterns may be used to map out and analyze usage and traffic of different areas of a shopping space over time to provide a better understanding of customer shopping patterns and habits.

In some embodiments, the central computer system 130 is further configured to estimate a store worker's location by comparing data obtained from a handheld device carried by the store worker with previously stored scan data relating to retail products throughout the store, which may include storage and/or shelf location data associated with various retail products sold in the shopping facility. The handheld device carried by the store worker may comprise, for example, a personal computer, a laptop computer, or a handheld electronic communication device such as a mobile phone or tablet or the like, and may be communicatively coupled to the central computer system 130. In some embodiments, the handheld device may be capable of scanning product identification data from retail products throughout the shopping facility, which may be stored in database 140. In some embodiments, the store worker's handheld device may include a geolocation and/or global positioning component that transmits the location of the handheld device to the central computer system 130.

The central computer system 130 may be further configured to estimate the store worker's path of travel by comparing successive scans from the handheld device carried by the store worker with the stored scan data. In some embodiments, the central computer system 130 may be further configured to determine if the store worker is present when the light emitter is activated by comparing the store worker's location to data obtained from the light detector 150 and location data associated with the light emitter 120, which allows the system to subtract and/or ignore light emissions attributed to store workers when estimating customer traffic patterns. In some embodiments, the store worker's last known location and/or path of travel may be stored in database 140.

In some embodiments, the system may be configured to detect luminescence from one or more customers and/or store workers in the shopping facility using, for example, thermal imaging techniques. For example, the system may include a thermal imager, such as an FLIR camera, for this purpose. The thermal imager may comprise the light detector 150, or the thermal imager may be a separate component coupled to the system. Using the thermal imager, the system may be configured subtract or otherwise filter out luminescence contributed by one or more store workers (or customers) in the shopping facility. Thermal imaging techniques, such as FLIR, may also be used to distinguish between customers and store workers present in the shopping facility.

The database 140 generally comprises volatile and/or non-volatile computer readable storage memory device(s). While the database 140 is shown as a separate component from the memory 132 of the central computer system 130 in FIG. 1, in some embodiments, the database 140 and the memory 132 may be implemented with the same one or more memory devices. In some embodiments, the database 140 may comprise multiple databases. Data stored in the database 140 may be organized in one or more database tables (data structures) comprising rows and columns. The database 140 may generally store data obtained from the light detector 150, as well as location information associated with one or more light emitters 120. In some embodiments, the database 140 may further store scan data, which may include storage and/or shelf location data associated with various retail products sold in the shopping facility. The database 140 may further store information related to store workers, such as, for example, last known locations of store workers and/or location histories of store workers. In some embodiments, database 140 may store data related to estimated customer traffic patterns.

Figure 2:
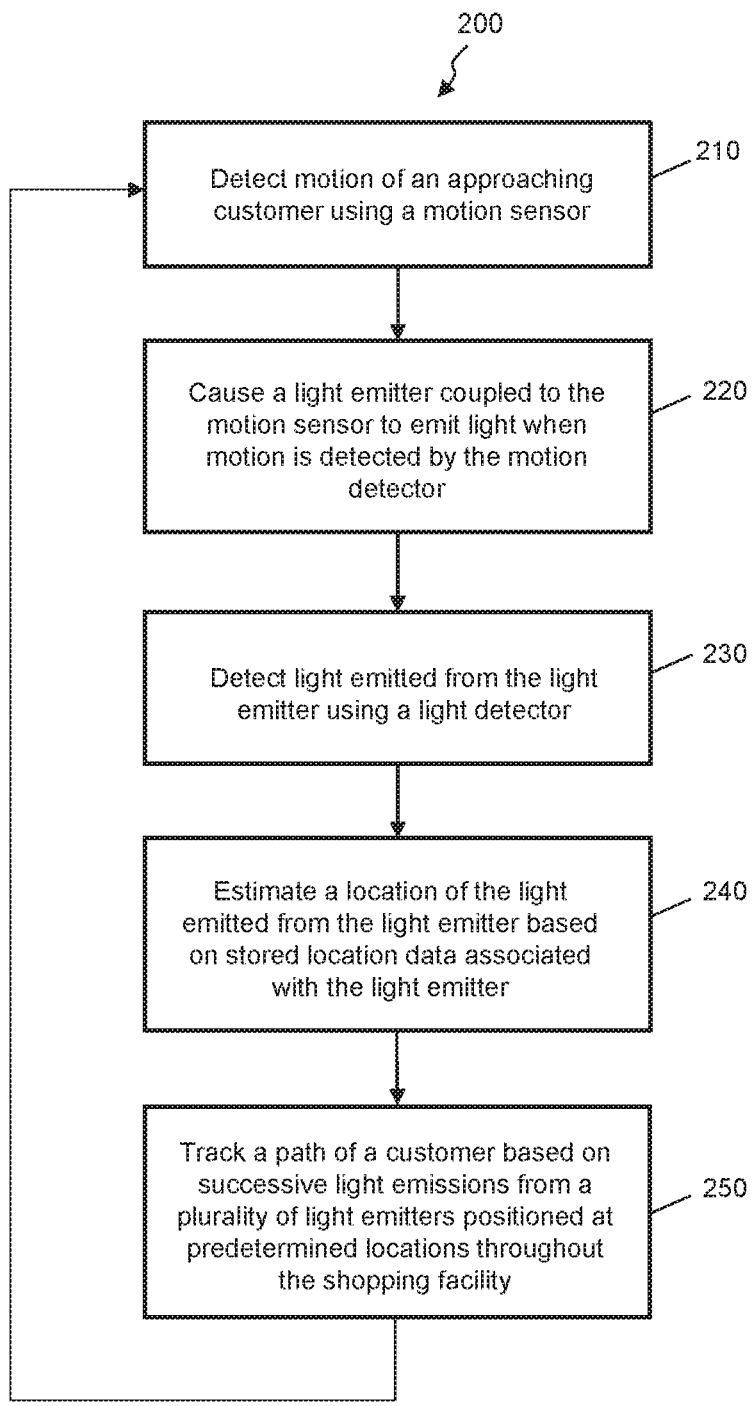
FIG. 2 is a flow diagram of a method in accordance with several embodiments.

Referring now to FIG. 2, a method for detecting traffic in a shopping facility is shown. Generally, the method shown in FIG. 2 may be implemented with a processor based device such as a control circuit, a central processor, and the like. In some embodiments, the method shown in FIG. 2 may be implemented with the central computer system 130 in FIG. 1.

In step 210, the system detects motion of an approaching customer using a motion sensor. In some embodiments, the motion sensor may comprise the motion sensor 110 described with reference to FIG. 1. The motion sensor may be configured to detect motion from an approaching person within a predetermined distance using any active or passive motion sensing technology, such as, for example, infrared, ultrasonic, microwave, and combinations thereof. The motion sensor may be positioned in any location in a shopping facility. For example, the motion sensor may be installed in the ceiling, pillars, beams, modules, display shelves, etc. of a shopping facility.

In step 220, a light emitter coupled to the motion sensor emits a light signal when motion is detected by the motion sensor. In some embodiments, the light emitter may comprise the light emitter 120 described with reference to FIG. 1. The light emitter may be coupled to the motion sensor via a wired and/or wireless signal connections. In some embodiments, the light emitter may be integrated with the motion sensor. In some embodiments, the light emitter and the motion sensor may be battery powered. The light emitter may be configured to emit any color or wavelength of visible light or non-visible light. In some embodiments, the light emitter may be configured to emit different wavelengths of light based on the number of customers the motion sensor detects at any given time. For example, when a first customer approaches the motion sensor, the light emitter may emit a first wavelength of light. When a second customer approaches the motion sensor while first customer is still present, the light emitter may emit a second wavelength of light in place of, or in addition to, the first wavelength of light. In some embodiments, the light emitter may be configured to emit different patterns of light based on the number of customers the motion sensor detects at any given time. In some embodiments, for example, in low traffic areas of the store, the light emitted from the light emitter may be visible light and may be positioned to illuminate one or more retail products adjacent to the light emitter when motion is detected by the motion sensor. In some embodiments, the light emitter may be configured to emit light for a predetermined length of time. In other embodiments, the light emitter may be configured to emit light for a length of time that the motion sensor detects a continuous motion. The light emitter may be positioned in any location in a shopping facility. For example, the light emitter may be installed in the ceiling, pillars, beams, modules, display shelves, etc. of the shopping facility. Some embodiments may include a plurality motion sensors coupled to a plurality of light emitters positioned at predetermined locations throughout the shopping facility. In some embodiments, each light emitter in the plurality of light emitters may emit one or more different wavelengths of light such that each location of each light emitter is associated with one or more different wavelengths of light.

In step 230, the system detects light emitted from the light emitter using a light detector. In some embodiments, the light detector may comprise the light detector 150 described with reference to FIG. 1. The light detector may generally be configured to capture light in a shopping facility and may comprise any luminosity detector or imaging device that is capable of detecting light. In some embodiments, the light detector may comprise a video imaging device. The light detector may have a field of view including the light emitter. In some embodiments, the light detector may comprise an array of light detectors positioned throughout the shopping facility, which may, in some cases, detect one or more different wavelengths of light. The light detector may comprise stationary light detectors installed in the shopping facility. For example, the light detector may be installed in the ceiling, pillars, beams, modules, display shelves, etc. of a shopping facility. In some embodiments, the light detector may be configured to detect specific wavelengths of light which may be emitted from the light emitter.

In step 240, the system automatically estimates, using a control circuit, a location of the light emitted from the light emitter based on location data associated with the light emitter, which may be stored in a database, such as for example, database 140 described with reference to FIG. 1. The system may process the data collected by the light detector and compare the data to stored location data associated with the light emitter to estimate a location of the light emitter, thereby allowing the system to ascertain the presence and location of one or more customers in the vicinity of the light emitter.

In step 250, the system automatically tracks a path of a customer based on successive light emissions from a plurality of light emitters positioned throughout the shopping facility. For example, as a customer approaches a first aisle in a shopping facility, a first light emitter may emit a first light in response to the approaching customer. The light emitted from the first light emitter may be, for example, a short burst of light, or the light emitter may remain lit for as long as the motion sensor coupled to the light emitter detects motion from the customer. When the customer moves from the first aisle to a second aisle, a second light emitter may emit a second light in response to the approaching customer. The light detector captures the light emissions from the first and second light emitters and estimates the locations of the first and second light emitters based on stored location data, allowing the system to track the customer throughout the store. The system may determine the location of each light emitter based, for example, on the variance in each of the emitted light's spectra, strobe rate, and the like, which may be stored in one or more databases. In some embodiments, the system may estimate a location of one or more light emitters using a video imaging device, which may determine a distance and source of the emitted light for each light emitter. In some embodiments, the video imaging device may be the light detector. The estimated location(s) of the one or more light emitters may be stored in the video imaging device and/or in one or more databases. In cases where each light emitter emits one or more different wavelengths of light, the system may automatically determine the location of each light emitter based on known locations associated with each wavelength of light.

In some embodiments, the system may estimate customer traffic patterns in an area adjacent to the light emitter based at least on how often the light emitter is activated to emit light. In some embodiments, the system may estimate customer traffic patterns and/or customer density based on the number of different wavelengths and/or patterns of light emitted from one or more light emitters at any given time or during any given duration.

In some embodiments, the system may be further configured to estimate dwell time of a customer based on the length of time that the light emitter emits light. In cases where each light emitter emits one or more different wavelengths of light, the system may automatically determine the location of each light emitter based on known locations associated with each wavelength of light. In some embodiments, the customer's path of travel may be stored in a database.

In some embodiments, the routes of customers may be analyzed by the system to generate one or more alerts and/or tasks. For example, the system may determine one or more heavy traffic areas and instruct a motorized unit and/or a store associate to survey the area to ensure the area is clean and/or sufficiently stocked. In another example, the system may determine one or more areas with unusually low traffic and instruct a motorized unit and/or a store associate to investigate for the presence of spills or other type of obstructions. In some embodiments, the system may aggregate a plurality of customer traffic routes to determine sections needing attention.

In some embodiments, the system may compare customer traffic patterns with point of sale data to determine if the point of sale data correlates to the customer traffic patterns. For example, in some embodiments, the system may match the customer with a checkout receipt based on the time that the customer approaches a checkout terminal. The system may then compare the items purchased during that shopping trip with the route and the dwell time of the customer. If the customer dwells at a section for a set period of time but no item from that section of the store is purchased, the system may mark the section as a section needing attention. In some embodiments, the system may aggregate a plurality of estimated customer traffic patterns to determine sections needing attention. In some embodiments, the system may further provide a user interface for viewing and analyzing the estimated customer traffic patterns. In some embodiments, the system may cause user interfaces on user devices to display alerts and/or task assignments based on the analysis of the estimated customer traffic patterns.

In some embodiments, the system may estimate a store worker's location by comparing scan data obtained from a handheld device carried by the store worker with previously stored data relating to retail products throughout the store, which may include storage and/or shelf location data associated with various retail products sold in the shopping facility. The handheld device carried by the store worker may comprise, for example, a personal computer, a laptop computer, or a handheld electronic communication device such as a mobile phone or tablet or the like. In some embodiments, the handheld device may be capable of scanning product identification data from retail products throughout the shopping facility, which may be stored in a database. In some embodiments, the store worker's handheld device may include a geolocation and/or global positioning component that transmits the location of the handheld device to the system.

The system may also estimate the store worker's path of travel by comparing successive scans from the handheld device carried by the store worker with the stored scan data. In some embodiments, the system may be further configured to determine if the store worker is present when the light emitter is activated by comparing the store worker's location to data obtained from the light detector and location data associated with the light emitter, which allows the system to subtract and/or ignore light emissions attributed to store workers when estimating customer traffic patterns. In some embodiments, the store worker's last known location and/or path of travel may be stored in one or more databases.

In some embodiments, the system may be configured to detect luminescence from one or more customers and/or store workers in the shopping facility using, for example, thermal imaging techniques. For example, the system may include a thermal imager, such as an FLIR camera, for this purpose. The thermal imager may comprise the light detector 150, or the thermal imager may be a separate component coupled to the system. Using the thermal imager, the system may be configured subtract or otherwise filter out luminescence contributed by one or more store workers (or customers) in the shopping facility. Thermal imaging techniques, such as FLIR, may also be used to distinguish between customers and store workers present in the shopping facility.

After step 250, steps 210-250 may be repeated for each instances of detected motion to track traffic patterns. By repeating this process, the system may constantly track and update locations and paths of a plurality of customers in the shopping facility based on their location history.

Figure 3:
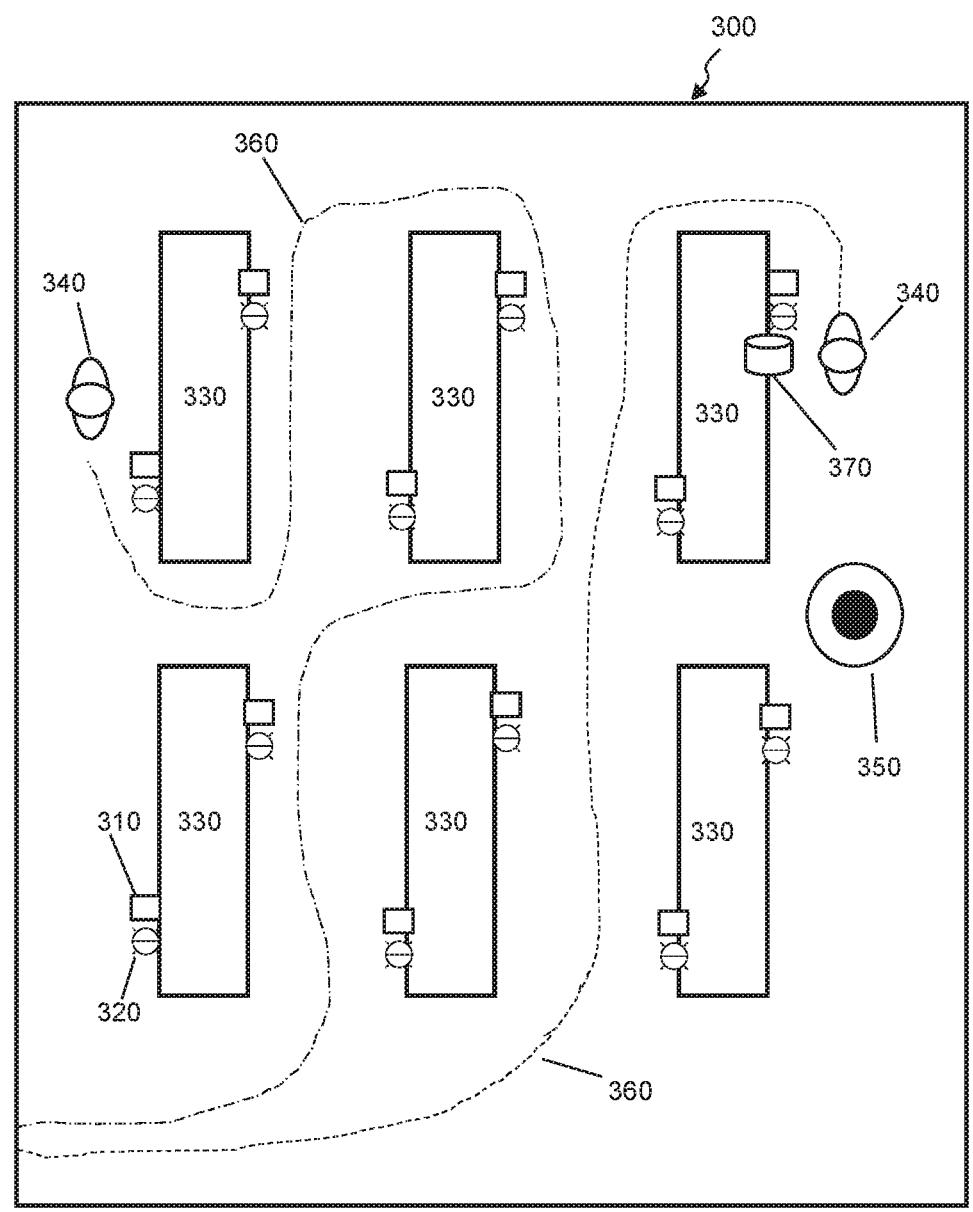
FIG. 3 is an illustration of a shopping facility in accordance with several embodiments.

Next referring to FIG. 3, an illustration of a shopping facility according to some embodiments is shown. The shopping space 300 comprises a plurality of display modules 330 (also known as "modular"), a light detector 350, and a plurality of motion sensors 310 coupled to light emitters 320 positioned throughout the shopping facility. When a customer 340 approaches a motion sensor 310 and is within a predetermined distance from the motion sensor 310, a light emitter 320 communicatively coupled to the motion sensor 310 emits a light signal. In some embodiments, the light emitter 320 and the motion sensors 310 may be battery powered. The light emitter 320 may be configured to emit any color or wavelength of visible light or non-visible light. In some embodiments, for example, in low traffic areas of the store, the light emitted from the light emitter 320 may be visible light and may be positioned to illuminate one or more retail products adjacent to the light emitter 320 when motion is detected by the motion sensor 310. In some embodiments, the light emitter 320 may be configured to emit different wavelengths of light based on the number of customers 340 the motion sensor 310 detects at any given time. For example, when a first customer 340 approaches the motion sensor 310, the light emitter 320 may emit a first wavelength of light. When a second customer 340 approaches the motion sensor 310 while first customer is still present, the light emitter 320 may emit a second wavelength of light in place of, or in addition to, the first wavelength of light. In some embodiments, the light emitter 320 may be configured to emit different patterns of light based on the number of customers 340 the motion sensor 310 detects at any given time. In some embodiments, the system may estimate customer traffic patterns and/or customer density based on the number of different wavelengths and/or patterns of light emitted from the one or more light emitters 320 at any given time or during any given duration.

In some embodiments, the light emitter 320 may be configured to emit light for a predetermined length of time. In other embodiments, the light emitter 320 may be configured to emit light for a length of time that the motion sensor detects a continuous motion. In some embodiments, each light emitter 320 in the plurality of light emitters may emit one or more different wavelengths of light such that each location of each light emitter 320 is associated with one or more different wavelengths of light. The light detector 350 may generally be configured to capture light in a shopping facility and may comprise any luminosity detector or imaging device that is capable of detecting light. In some embodiments, the light detector 350 may comprise a video imaging device.

When the light detector 350 detects light emitted from one or more light emitters 320 in the field of view of the light detector 350, the system may determine a location of the light emitter 320 based on previously stored known location data associated with the light emitter 320. In some embodiments, the system may estimate a location of each light emitter 320 using a video imaging device, which may determine a distance and source of the emitted light for each light emitter 320. In some embodiments, the video imaging device may be the light detector 350. The estimated location(s) of the one or more light emitters 320 may be stored in the video imaging device and/or in one or more databases. In some embodiments, the system may determine the location of each light emitter based, for example, on the variance in each of the emitted light's spectra, strobe rate, and the like, which may be stored in one or more databases. As the customer 340 approaches and passes a succession of light emitters 320, the customer's path 360 may be tracked based on successive light emissions from each light emitter 320 the customer passes. The light emitted from one or more light emitters 320 may also be used to selectively light specific areas of the shopping facility and/or specific retail products 370 as the customer approaches, thus saving energy and reducing energy-related costs. In embodiments where one or more light emitters 320 are configured to emit light for a length of time that the motion sensor 310 detects a continuous motion, the system may also estimate dwell time of a customer based on the length of time that the light emitter 320 emits light.

Over time, as customers 340 traverse the sales floor and their locations and paths 360 are estimated and tracked based on successive light emissions detected by the light detector 350, the system may aggregate the data to create customer traffic patterns and heat maps of activity throughout the store, which may be valuable for store management and marketing purposes.

In one embodiment, a system for detecting traffic in a shopping facility comprises: a plurality of light emitters positioned at predetermined locations throughout the shopping facility, each light emitter being coupled to a motion sensor configured to detect motion of an approaching customer such that the each light emitter emits light when motion of an approaching customer is detected by the motion sensor; a light detector having a field of view including at least one of the plurality of light emitters and configured to detect light from the at least one of the plurality of light emitters; a database configured to store data obtained from the light detector and location data associated with the plurality of light emitters; and a control circuit coupled to the light detector and the database, the control circuit configured to: obtain data from the light detector relating to light emitted from the plurality of light emitters; and estimate a location of the light emitted from the each of the plurality of light emitters based on location data associated with each of the plurality of light emitters stored in the database, and track a path of a customer based on successive light emissions from the plurality of light emitters.

In one embodiment, a method of detecting traffic in a shopping facility comprises: detecting motion of an approaching customer using a motion sensor; causing a light emitter coupled to the motion sensor to emit light when motion is detected by the motion sensor; detecting light emitted from the light emitter using a light detector; estimating, using a control circuit, a location of the light emitted from the light emitter based on location data associated with the light emitter stored in a database; and tracking a path of a customer based on successive light emissions from a plurality of light emitters positioned at predetermined locations throughout the shopping facility.

It should be understood that each of the components of the system described herein may be in communication with one another using any conventional communications protocol, including wireless communication protocols. Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system for detecting traffic in a shopping facility, the system comprising:
   a plurality of light emitters positioned at predetermined locations throughout the shopping facility, each light emitter being coupled to an associated motion sensor configured to detect motion such that each light emitter emits a light signal when motion of an approaching customer is detected by the associated motion sensor;
   a light detector having a field of view including the plurality of light emitters and configured to detect the light signals emitted from the plurality of light emitters;
   a database configured to store signal data obtained from the light detector and location data associated with the plurality of light emitters; and
   a control circuit coupled to the light detector and the database, the control circuit configured to:
      obtain the signal data from the light detector relating to the light signals emitted from the plurality of light emitters;
      estimate a location of the light signals emitted from the plurality of light emitters based on the location data associated with the plurality of light emitters stored in the database; and
      track a path of the approaching customer based on successive light signal emissions from at least two of the plurality of light emitters,
      wherein the control circuit is further configured to estimate a location of a store worker by comparing a scan from a handheld device carried by the store worker, the handheld device being coupled to the control circuit, with scan data stored in the database, and
      determine if the store worker is present when at least one of the plurality of light emitters is activated by the approaching customer by comparing the location of the store worker to the signal data obtained from the light detector and the location data associated with the at least one of the plurality of light emitters.

2. The system of claim 1, wherein the control circuit is further configured to estimate customer traffic patterns in an area adjacent to at least one of plurality of light emitters based at least on how often the at least one of the plurality of light emitters is activated to emit a light signal.

3. The system of claim 2, wherein the control circuit is further configured to compare the customer traffic patterns with point of sale data to determine if the point of sale data correlates to the customer traffic patterns.

4. The system of claim 1, wherein at least one of the plurality of light emitters is configured to emit light for a length of time that the motion sensor detects a continuous motion of the approaching customer, and the control circuit is further configured to estimate a dwell time of the approaching customer based on a length of time that the at least one of the plurality of light emitters emits the light signal.

5. The system of claim 1, wherein at least two of the plurality of light emitters emits a different wavelength of light.

6. The system of claim 1, wherein the light signal emitted from at least one of the plurality of light emitters is visible light configured to illuminate one or more retail products in the shopping facility.

7. The system of claim 1, wherein the light signal emitted from at least one of the plurality of light emitters is non-visible light.

8. The system of claim 1, wherein at least one of the plurality of light emitters is configured to emit a light signal for a predetermined length of time.

9. The system of claim 1, wherein the control circuit is further configured to estimate the store worker's path of travel by comparing successive scans from the handheld device carried by the store worker with scan data stored in the database.

10. A method for detecting traffic in a shopping facility, the method comprising:

detecting motion of an approaching customer using a motion sensor;

causing a light emitter coupled to the motion sensor to emit a light signal when motion is detected by the motion sensor;

detecting the light signal emitted from the light emitter using a light detector;

estimating, using a control circuit, a location of the light signal emitted from the light emitter and detected by the light detector based on location data associated with the light emitter stored in a database;

tracking a path of the approaching customer based on successive light signal emissions from a plurality of light emitters positioned at predetermined locations throughout the shopping facility estimating a location of a store worker by comparing a scan from a handheld device carried by the store worker with scan data stored in the database; and determining if the store worker is present when at least one of the plurality of light emitters is activated by the approaching customer by comparing the location of the store worker to signal data obtained from the light detector and location data associated with the at least one of the plurality of light emitters.

11. The method of claim 10, further comprising estimating customer traffic patterns in an area adjacent to the light emitter based on how often the light emitter is activated to emit the light signal.

12. The method of claim 11, further comprising comparing the customer traffic patterns with point of sale data to determine if the point of sale data correlates to the customer traffic patterns.

13. The method of claim 10, further comprising estimating dwell time of the approaching customer based on a length of time that the light emitter emits the light signal when the light emitter is configured to emit the light signal for a length of time that the motion sensor detects a continuous motion of the approaching customer.

14. The method of claim 10, further comprising estimating a path of travel of a store worker by comparing successive scans from a handheld device carried by the store worker with scan data stored in the database.

* * * * *